United States Patent [19]

Hirsch et al.

[11] Patent Number: 4,457,460

[45] Date of Patent: Jul. 3, 1984

[54] WRISTWATCH STRAP WITH PROTECTIVE LAYER THAT CONTACTS THE WRIST

[75] Inventors: Hermann Hirsch, Klagenfurt; Reinhart Jaresch, Vienna, both of Austria

[73] Assignee: Hermann Hirsch Leder- und Kunststoffwarenfabrik, Klagenfurt, Austria

[21] Appl. No.: 461,928

[22] Filed: Jan. 28, 1983

Related U.S. Application Data

[63] Continuation of Ser. No. 258,003, Apr. 27, 1981, abandoned.

[30] Foreign Application Priority Data

Nov. 3, 1980 [AT] Austria ................................ 5400/80

[51] Int. Cl.$^3$ ......................... A45C 11/10; B32B 1/04
[52] U.S. Cl. .................................... 224/178; 428/76; 428/68; 428/332; 428/328; 428/519; 428/458; 428/459; 428/473; 428/540; 428/543; 224/164
[58] Field of Search ................... 428/76, 68, 316, 332, 428/328, 518, 458, 459, 473, 540, 543; 224/178, 164

[56] References Cited

U.S. PATENT DOCUMENTS

| | | | |
|---|---|---|---|
| 1,797,583 | 3/1931 | Miller | 224/178 |
| 3,013,919 | 12/1961 | Bialy | 156/212 |
| 4,197,968 | 4/1980 | Ullmann et al. | 224/178 |
| 4,206,514 | 6/1980 | Yamauchi | 428/328 X |

*Primary Examiner*—P. Ives
*Attorney, Agent, or Firm*—Young & Thompson

[57] ABSTRACT

A wristwatch strap of leather or the like has a continuous non-porous barrier layer on the surfaces of the strap that contact the wrist of the wearer. The barrier layer consists of metal particles such as aluminum, noble metal or silver, having a particle size of 150 to 500 microns, preferably 200 to 350 microns, embedded in a matrix which consists of a synthetic resin. The barrier layer is effective to prevent the transfer of allergens and irritants from the material of the wristwatch strap, to the skin of the wearer.

6 Claims, No Drawings

WRISTWATCH STRAP WITH PROTECTIVE LAYER THAT CONTACTS THE WRIST

This application is a continuation of application Ser. No. 258,003, filed Apr. 27, 1981, now abandoned.

This invention relates to an article which consists preferably of flexible material and is intended to be used in direct contact with the skin or mucous membrane of a wearer.

Certain materials are known to contain allergens or irritants, which when articles made from such materials are worn by persons having an easily irritable skin may cause unpleasant irritations of the skin and/or allergies. Said materials include leather and leatherlike materials, which are used to make, e.g., gloves, sweatbands for hats or helmets, watch straps and orthopedic articles. Similar remarks are applicable to films or woven fabrics made of synthetic resins and to rubber and rubberlike materials, also to various materials used to make articles of clothing or bandages etc., and to some materials used for medical purposes.

It is an object of the invention so to improve an article made from such materials that an irritation of the skin and/or allergies will be precluded whereas the wearability of the article will not be adversely affected.

This object is accomplished according to the invention in that at least on that side of the article which is intended to be in contact with the skin or a mucous membrane of the wearer the article is provided with a barrier layer which will prevent a transfer of allergens and/or irritants from the substrate material onto or into the skin or mucous membrane of the wearer. That barrier layer consists of a metal, preferably aluminum or a noble metal, particularly silver, or of particles of metal, preferably aluminum or a noble metal particularly silver, which particles are embedded in a matrix consisting of a binder.

The barrier layer provided in accordance with the invention prevents a direct contact of the substrate material of the article with the skin or mucous membrane of the wearer. The barrier layer assists the function of the horny layer of the cuticle. That horny layer is thinner in certain regions of the human skin, e.g., at the wrist, where wrist watches are worn, or on the forehead or at the hip. The barrier layer also prevents an ingress of allergens and/or irritants into deeper layers of the skin and pevents also an ingress of moisture into the article, e.g., when leather straps (watch straps) are worn during bathing or when the wearer sweats during physical exercize. Sweat can dissolve allergens out of materials and this will often initiate the sensitization. For this reason this function to prevent an ingress of moisture is of high significance. The layer may also improve the mechanical properties of the article, e.g., its resistance to wear.

Within the scope of the invention, the use of thin layers consisting of varnishes which contain metal powders has proved particularly satisfactory. The metal particles of themetal powder have preferably the same particle size as the metal particles in the known bronze pigments, which are used as gloss-imparting pigments in paints.

The metal particles contained in the barrier layer may preferably consist of aluminum or a noble metal, particularly pure silver.

The barrier layer may have a thickness of 150 to 500 microns. Preferred thickness values lie between 200 and 350 microns.

The barrier layer may be bonded to the substrate material by a bonding layer. The bonding layer may consist of a layer of synthetic resin, e.g., a varnish layer. That bonding layer will substantially close or fill any voids or recesses on the surface of the material so that the latter can be provided with a substantially continuous coating. The bonding layer may differ in color from the barrier layer and will then warn the wearer that the barrier layer preventing a transfer of allergens and/or irritants has been worn off.

An important field of application of the invention is watch straps made of genuine leather or of leatherlike materials.

What is claimed is:

1. A flexible wristwatch strap of leather or the like, having a continuous nonporous barrier layer on the surfaces of the wristwatch strap that contact the wrist of the wearer, said barrier layer consisting of metal particles embedded in a matrix which consists of a synthetic resin.

2. A flexible wristwatch strap as claimed in claim 1, wherein said metal particles are aluminum.

3. A flexible wristwatch strap as claimed in claim 1, wherein said metal particles are a noble metal.

4. A flexible wristwatch strap as claimed in claim 1, wherein said metal particles are silver.

5. A flexible wristwatch strap as claimed in claim 1, wherein said metal particles have a particle size of 150 to 500 microns.

6. A flexible wristwatch strap as claimed in claim 1, wherein said metal particles have a particle size of 200 to 350 microns.

* * * * *